(12) United States Patent
Troukhan et al.

(10) Patent No.: US 10,482,992 B2
(45) Date of Patent: Nov. 19, 2019

(54) GENOME BROWSER

(71) Applicant: Ceres, Inc., Thousand Oaks, CA (US)

(72) Inventors: Maxim Troukhan, Agoura Hills, CA (US); Stanislav Freidin, Encino, CA (US); Nickolai Alexandrov, Thousand Oaks, CA (US); Timothy Swaller, Newbury Park, CA (US)

(73) Assignee: CERES, INC., Thousand Oaks, CA (US)

(*) Notice: Subject to any disclaimer, the term of this patent is extended or adjusted under 35 U.S.C. 154(b) by 712 days.

(21) Appl. No.: 14/991,392

(22) Filed: Jan. 8, 2016

(65) Prior Publication Data

US 2016/0203195 A1    Jul. 14, 2016

Related U.S. Application Data

(60) Provisional application No. 62/101,735, filed on Jan. 9, 2015.

(51) Int. Cl.
　　*G01N 33/48*　　(2006.01)
　　*G16B 30/00*　　(2019.01)
　　*G16C 99/00*　　(2019.01)

(52) U.S. Cl.
　　CPC ............. *G16B 30/00* (2019.02); *G16C 99/00* (2019.02)

(58) Field of Classification Search
　　None
　　See application file for complete search history.

(56) References Cited

U.S. PATENT DOCUMENTS

2010/0281401 A1    11/2010    Tebbs et al.
2014/0282177 A1    9/2014    Wang et al.

OTHER PUBLICATIONS

Kuhn et al. (The UCSC Genome Browser and Associated Tools, Briefings in Bioinformatics, 2012, vol. 14, No. 2, 144-161.*
Krol (Persephone, the Real-Time Genome Browser, Apr. 25, 2014, Bio-IT World, http://www.bio-itworld.com/2014/4/25/persephone-real-time-genome-browser.html, 1-4.*
Zweig et al. (Genomics, 2008, 92, 75-84).*
Ma et al. (PLoS ONE, Mar. 2012, vol. 7, Iss 3, 1-11).*

\* cited by examiner

*Primary Examiner* — Larry D Riggs, II
(74) *Attorney, Agent, or Firm* — Dentons US LLP

(57) ABSTRACT

This document describes, among other things, a computer-implemented method for displaying and analyzing sequenced genome data. The method can include obtaining, at a computing system, genomic data for a plurality of organisms. A graphical representation can of the genomic data can be generated by the computing system based at least on the genomic data for the plurality of organisms, and the graphical representation can include a plurality of tracks that are arranged to show one or more features of the genomic data for different ones of the plurality of organisms. The graphical representation can be output for display by the computing system.

52 Claims, 10 Drawing Sheets

GENOME BROWSER

CROSS-REFERENCE TO RELATED APPLICATIONS

This application claims the benefit of priority under 35 U.S.C. § 119(e) to U.S. Application Ser. No. 62/101,735, filed Jan. 9, 2015, the entire contents of which are hereby incorporated by reference in their entirety.

TECHNICAL FIELD

This document generally relates to computer-implemented systems, methods, and other techniques for analyzing and representing genome-related biological data.

BACKGROUND

A very large amount of genome-related biological data is becoming available to researchers, oftentimes generated with technologies such as next generation sequencing (NGS) and microarrays. In addition, there is much genome-linked public and sometimes proprietary information related to phenotypes and genotypes of individual organisms, including polymorphic markers, quantitative trait loci (QTL), tissue expression levels and regulation of individual genes, characterized mutations, somatic genomic alteration, and clinical trial results such as pharmaceutical efficacy and toxicology studies. Additional data comes from automated analyses, but insights are ultimately gained by human understanding and judgment of the implications of underlying information.

SUMMARY

This document generally provides systems, methods, and other techniques for analyzing and representing genome-related biological data.

Some implementations include a computer-implemented method for displaying and analyzing sequenced genome data. The method can include obtaining, at a computing system, genomic data for a plurality of organisms. A graphical representation of the genomic data can be generated by the computing system based at least on the genomic data for the plurality of organisms, and the graphical representation can include a plurality of tracks that are arranged to show one or more features of the genomic data for different ones of the plurality of organisms. The plurality of tracks can include a first track that shows a first particular feature of a first organism, a second track that shows the first particular feature of a second organism, and a third track that shows the first particular feature of a third organism. The method can include identifying that the first organism is designated as a reference organism, and in response, ordering the plurality of tracks in the graphical representation of the genomic data so that the first track that shows the first particular feature of the first organism is shown in a reference position of the graphical representation, the second and third tracks are shown in respective positions outside of the reference position, and the first particular features of the second and third tracks are each shown relative to the first particular features of the first track. The graphical representation can be outputted for display by the computing system.

These and other implementations can optionally include one or more of the following features.

The graphical representation of the genomic data can be a first graphical representation of genomic data of a first chromosome. The computing system can generate a second graphical representation of genomic data of a different, second chromosome, the second graphical representation including one or more tracks that are arranged to show one or more features of the genomic data of the second chromosome for at least one organism, and the computing system can output the second graphical representation for display.

The computing system can determine syntenic regions of the genomic data of the first chromosome and the genomic data of the second chromosome, and can output for display graphical elements that connect the first graphical representation and the second graphical representation. The graphical elements can show corresponding syntenic regions of the genomic data of the first chromosome and the genomic data of the second chromosome.

The computing system can identify that user input has entered a search query associated with a particular organism, and in response, can obtain a set of search results that are determined to be relevant to the search query. The search results in the set can indicate respective sequence locations, such as in a chromosome, for the particular organism.

The computing system can generate, and output for display, a graphical representation of one or more chromosomes for the particular organism that shows graphical markers at locations of the one or more chromosomes that correspond to the respective sequence locations (e.g., chromosomal sequence locations) indicated by the search results in the set of search results.

The computing system can receive an indication that user input selected a first search result from among the set of search results, and in response, can automatically generate and output for display a graphical representation of the genomic data for the particular organism that shows a zoomed-in region corresponding to the location of the chromosome indicated by the first search result.

The computing system can receive an indication that the designation of the reference organism is changed from the first organism to the second organism, and in response to receiving the indication that the designation of the reference organism is changed, can perform a re-ordering of the plurality of tracks in the graphical representation of the genomic data. The re-ordering can be performed so that the second track that shows the first particular feature of the second organism is shown in the reference position of the graphical representation, the first and third tracks are shown in respective positions outside of the reference position, and the first particular features of the first and third tracks are each shown relative to the first particular features of the second track. The computing system can then output the re-ordered graphical representation of the genomic data for display.

Reordering the plurality of tracks in the graphical representation can include automatically arranging the plurality of tracks in descending order of determined genetic similarity between the second organism, due to the second organism being designated as the reference organism, and the corresponding organisms for each of the other tracks in the plurality of tracks, so that tracks corresponding to organisms that are more genetically similar to the second organism are caused to be shown in closer proximity to the second track, and tracks corresponding to organisms that are less genetically similar to the second organism are caused to be shown a further distance from the second track.

The computing system can determine the genetic similarities between the second organism and the corresponding organisms for each of the other tracks in the plurality of tracks based only on data for a portion of the chromosomal sequence of the organisms that is currently being outputted for display. The genetic similarities can also be determined based on data from the entire sequence, rather than just a portion of the sequence.

At least one of the plurality of tracks in the graphical representation can show a linear representation of codons in a chromosome sequence of an organism.

At least one of the plurality of tracks can be an mRNA track that shows locations of transcribed regions of the chromosome sequence.

The first particular feature can include single nucleotide polymorphisms (SNPs), and the computing system can further generate the graphical representation of the genomic data so that the second track shows, as a result of the first organism being designated as the reference organism, SNPs in the genomic data of the second organism relative to the genomic data of the first organism shown in the first track.

The second track can show SNPs in the genomic data of the second organism relative to the genomic data of the first organism by showing distinctive colored elements along the second track at locations that correspond to locations in a chromosome sequence where SNPs occur that are opposite of SNPs in the genomic data of the first organism.

The computing system can obtain data that indicates expression levels for corresponding portions of the genomic data for one or more of the plurality of organisms.

The first particular feature can include the expression levels for the corresponding portions of the genomic data, and the computing system can further generate the graphical representation of the genomic data so that the second track shows, as a result of the first organism being designated as the reference organism, expression levels for the corresponding portions of the genomic data of the second organism relative to the expression levels of for the corresponding portions of the genomic data of the first organism.

The second track can show allele-specific expression levels.

The computing system can generate, based at least on the data that indicates the expression levels for the corresponding portions of the genomic data for the one or more of the plurality of organisms, a multidimensional plot showing variability in expression levels among different sets of expression data for particular ones of the plurality of organisms. The multidimensional plot can be outputted for display.

Generating the multidimensional plot can include automatically limiting the plot to showing only expression levels of sequences corresponding to a portion the genomic data being outputted for display in the graphical representation of the genomic data, to the exclusion of expression levels of sequences outside of the portion of the genomic data being outputted for display in the graphical representation of the genomic data.

The first particular feature can include at least one of quantitative trait loci (QTLs) and trait linkage scores for particular sequence locations.

The first particular feature can include CpG islands, and the computing system can further generate the graphical representation of the genomic data so that at least one of the plurality of tracks shows locations of CpG islands within the genomic data for a corresponding organism.

The plurality of tracks can include a fourth track that shows the first particular feature of a fourth organism. The computing system can further perform operations that include identifying that the fourth organism is designated as a second reference organism; and ordering, in response to identifying that the fourth organism is designated as the second reference organism and further based on the first organism being designated as the reference organism, the plurality of tracks in the graphical representation of the genomic data so that the fourth track is shown in a second reference position of the graphical representation, and the first particular features of the second and third tracks are each shown relative to both the first particular features of the first track and the first particular features of the fourth track.

The first and fourth organisms can be ancestors of the second and third organisms.

The plurality of tracks can be arranged to be displayed parallel to each other and can be arranged to synchronously show corresponding portions of a chromosome sequence.

Identifying that the first organism is designated as the reference organism can include receiving an indication that user input selected a control associated with the first track or the first organism.

At least one of the plurality of tracks in the graphical representation of the genomic data can show a representation of recombination frequency in a chromosome sequence of an organism.

Some implementations of the techniques described herein can be provided as a computing system including one or more processors, and/or as a computer program product comprised of instructions that are stored on one or more computer-readable devices, which may be transitory or non-transitory. When the instructions are executed by one or more processors, operations can be performed that correspond all or some of the stages in the method described in the preceding paragraphs.

Some implementations can include a computer program product, stored on one or more non-transitory computer-readable devices, for analyzing and representing genome-related biological data. The program product can include a genotype tracks module, a similarity analyzer, and a track arrangement module. The genotype tracks module can be configured to generate and output for display one or more tracks showing features of genomic data for corresponding organisms. The similarity analyzer can be configured to determine similarities between corresponding portions of genetic sequences for a reference organism and two or more additional organisms. The track arrangement module can be configured to order the one or more tracks for display based on the determined similarities between the corresponding portions of genetic sequences for the reference organism and the two or more additional organisms. In some implementations, the computer program product further include a search module configured to receive queries from user input, and to identify search results that are determined to be responsive to the queries in that the search results correspond to candidate locations in a chromosomal sequence for particular organisms associated with the queries. A graphical representation of the chromosomes along with markers for the identified sequence locations indicated by the search results can be generated when a search is performed in response to a user-entered query.

Particular implementations of the systems, methods, and other techniques described herein may realize none, one or more of the following advantages. An intuitive user interface can be provided that enhances the usability and analytical capabilities of a genome browser. Genome-related data can be graphically presented in a manner that facilitates identification of associations, for example, between genotypes and phenotypes of one or more organisms. A user can manually or automatically re-arrange multiple tracks that show different features of genome-related data, and the tracks can display features with respect to the features of a reference organism. For example, where an opposite single nucleotide polymorphism (SNP) appears in a first organism sample relative to a reference organism sample, a visual element can mark the location of the SNP in a chromosomal sequence. Different reference organisms can be designated, and a plurality of tracks can be manually or automatically re-arranged based on when the designation of the reference organism is updated. Users can quickly and easily access information of interest by searching annotated genome-related data to identify locations in one or more chromosomes for an organism in which candidate locations determined to be potentially relevant to a search query are found.

BRIEF DESCRIPTION OF THE DRAWINGS

Like reference numbers and designations in the various drawings indicate like elements.

DETAILED DESCRIPTION

This document generally provides computer-implemented systems, methods, and other techniques for analyzing and representing genome-related biological data. In some implementations, such techniques can be provided in a genome browser that includes visualization tools for generating and displaying graphical representations of sequenced genomes and sequence location-linked information. Genome browsers and the techniques described herein can provide significant benefits to researchers and others who work with genome-related biological data. For example, genome browsers can allow researchers to overcome problems associated with experimental results involving biological data, including problems of data quality resulting from human and instrument error. Moreover, sample sets of experiments or studies may be too small for definitive conclusions, and normalizing and comparing differently obtained large data sets, such as transcription levels or alterations, can be especially difficult in the absence of analytical tools such as a genome browser. As a result, false negative or positive associations sometimes need to be distinguished from reliable information. Consequently, the significance of disparate sources of available data always needs to be analyzed and interpreted by researchers investigating various aspects of biology.

The techniques described herein can permit researchers to analyze and interpret such genome-related biological data more efficiently and reliably than by conventional techniques. For example, some implementations of a genome browser according to the techniques described herein provide enhanced capabilities allowing users to view, arrange, and process available data in ways in which it may reveal or disprove apparent associations. The genome browser may also provide intuitive access to many data sources, and may provide analytical capabilities for the genomic information being visualized, which can be critical to gaining new insights in an investigation into biological interactions of interest.

Figure 1:
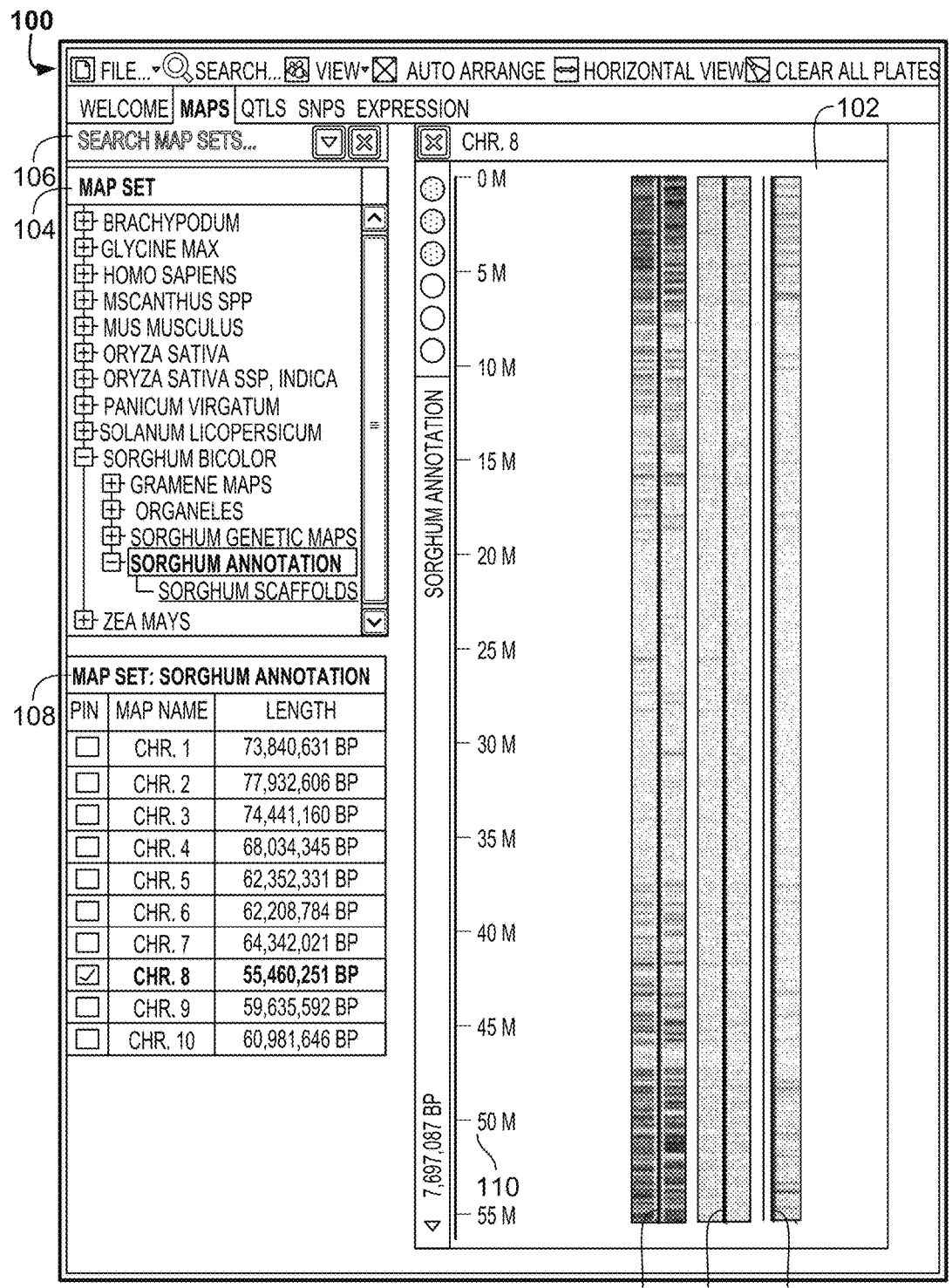
FIG. 1 depicts an example user interface of a genome browser including a browsing plate window showing genomic data for *Sorghum*.

Referring to FIG. 1, an example user interface 100 of a genome browser is shown that includes a browsing plate window 102 showing genomic data for a particular *Sorghum* chromosome. The user interface 100 includes a number of features that can permit data associated with many different organisms to be easily and efficiently accessed, loaded, and represented to a user. For example, FIG. 1 includes a browser plate component 102, a map set component 104, a map search component 106, and a chromosome map selection component 108.

The browser plate component 102 shows a graphical representation of genomic data for a selected organism. In this example, the genomic data is for chromosome 8 of a particular species of *Sorghum*. Other organisms can be selected for display in the browser plate component 102 as well. Thus, maps for different individuals, or even data for different tissue samples from a particular individual may be loaded and graphically represented in the browser plate component 102 for distinct organisms. In this way, genomic data for a single organism, or for multiple organisms, can be visually represented to the user. When multiple organisms are selected for inclusion in the browser plate component 102, as described further below, the data can be presented in a manner that emphasizes similarities and differences among the genomic data of the multiple organisms. Moreover, the data can be presented synchronously so that data associated with corresponding locations in a genomic sequence are presented in a coordinated fashion among each of the multiple organisms. In this way, for example, the user may focus on a particular location or region of a chromosome, and compare one or more features of the genomic data of multiple organisms. In this document, genomic data generally refers to any genome-related biological data, and can particularly include data that is tied to locations in a genomic sequence. For example, the genomic data may indicate features of the selected organisms such as sequence locations, descriptions, or other indications of (or combinations of these) codons, mRNA transcripts, genes, polymorphisms, gene expression levels, quantitative trait loci, and more. Genomic data may include indications of genotypes, but is not limited to genotypes.

By way of example, the browser plate component 102 shown in FIG. 1 of the *Sorghum* chromosome includes three vertical, parallel tracks 112*a-c*. Different features of the *Sorghum* chromosome are shown on each of the tracks. A first track 112*a* shows locations of codons in the chromosome sequence. A second track 112*b* shows the locations of mRNAs, and a third track 112*c* shows the locations of single nucleotide polymorphisms (SNPs) occurring in the sequence. Each of the features shown on the tracks is shown at locations in the browser plate 102 that correspond to their locations in the *Sorghum* chromosome sequence. A scale 110 at the leftmost side of the browser plate 102 shows a linear representation of the selected chromosome, in terms of base-pair (bp) locations. The lowest numbered base-pairs are shown at the top of the browser plate 102, and ascend to the highest numbered base-pairs toward the bottom of the browser plate 102.

The user interface 100 may provide controls that allow a user to configure the presentation of the browser plate 102. For example, the number of tracks may be adjusted, and the order of the tracks may similarly be changed at a user's command. A user may select which features of the genomic data to show in the browser plate 102. The user may zoom-into and out of particular portions of the chromosome sequence to view the features with finer resolution and/or greater detail in those portions of the sequence. For example, a user may use a mouse wheel to zoom in and out, and may scroll the browser plate image to any location of interest to view the features at that portion in greater detail (i.e., to zoom into the selected portion).

In some implementations, distinct colors can be assigned to each track that is shown in the browser plate 102. For example, the features shown by the first track 112*a* may be presented with purple markers, the features shown by the second track 112*b* may be presented with green markers, and the features shown by the third track 112*c* may be presented with black markers. The colors may be assigned by default according to pre-defined settings, or may be assigned by the user. Different colors may be associated with different features (e.g., codons by default are always shown in purple, while mRNAs by default are always shown in green). In some implementations, different colors may be associated with different organisms (e.g., features from a first tissue sample are assigned a first color set, while features from a second tissue sample are assigned a second color set).

The user interface 100 can also provide various additional features that allow data to be loaded and graphically represented in a browser plate 102. For example, the map set component 104 provides a list of maps that have been identified by the genome browser, and which a user may select to access the genomic data associated with each map. The maps may be organized and presented in a manner suitable for efficient navigation. FIG. 1 shows map sets organized alphabetically by different species of organisms, for example. The map sets are also provided in an expandable tree structure that allows users to select different categories of maps (e.g., different species of organisms), and then to select maps from within one or more sub-categories.

Thus, to access the *Sorghum* chromosome from the map set component 104, a user can scroll to and expand the *Sorghum bicolor* listing, access the *Sorghum* annotation sub-category. Genomic data may also be displayed as scaffolds, as it may be available in some cases before its definitive assembly into contiguous chromosomes. In some implementations, the map sets may also be searchable using map search component 106. When a user submits a query through the map search component 106, the genome browser identifies one or more search results that are determined to be relevant to the query. For example, if a user enters a species or genus name, the search component 106 may identify all maps that specify sequences containing the searched organism. Once a map set is identified, a specific map may be chosen within the chromosome map selection component 108. For example, ten different maps are included in the *Sorghum* map set, one for each of ten chromosomes. The user may select one of these maps, which can then cause the window for the browser plate component 102 to be populated and displayed with genomic data specified by the selected map.

In some implementations, screen graphics rendering of chromosomes and associated features can be zoom level dependent, i.e. with different levels of detail rendered as a user zooms in and out of a genomic region. For some features, two detail levels may be sufficient. For example, coding regions may be represented at low resolution as simple blocks of a length corresponding to gene length as aligned to the genomic area, while at high resolution their intron-exon structure and coding strand are represented. Other genomic features that may be very frequent in some regions, such as SNPs, can have multiple levels of detail representations. For example, at the lowest level of resolution they may be shown as a heat map of the density histogram indicating how dense or sparse the available features are. At medium resolution the features may be shown as sample blocks of underlying genomic regions, representing calculated values of all corresponding features, such as feature density and relatedness to a corresponding sample block of a reference individual. Finally, at the highest resolution the precise location, identifiers, or clickable links of individual features are rendered fully visible or functional.

The genome browser is designed to minimize the delay between the moment when the user selects a set of data to view, such as SNPs or quantitative data, and the moment when the data appears on the screen. In some implementations, the genome browser reduces such delay by a combination of pre-processing and selective loading processes.

All data for a single chromosome or some other biological sequence to be displayed such as a scaffold, is pre-processed for database storage and retrieval as follows. First, the data is broken up into pieces of uniform length, referred to as "tiles." Then, every tile is down-sampled to produce a low-resolution version of that tile (excluding those tiles that contain too few data points for sampling), using a sampling technique appropriate for the respective tile data. The sampling technique produces summary information that is recorded for each tile. For example, the summary information may be the number of SNPs in the tile, the minimum and/or maximum quantitative value inside the tile, or other appropriate summary of the data contained in the respective tile. Then, all tiles are encoded using a custom compression technique: instead of storing the full value for each data point, the genome browsing system stores instead its offset from the previous data point (or from the starting position of the tile if there is no previous data point), thus reducing the number of bits required for storage and transfer. Finally, these encoded bytes are compressed using standard compression algorithms such as GZip or LZ4. The compressed tiles are stored in the database, and retrieved and transferred in response to a user request.

In some implementations, the genome browser user interface can allow users to select the chromosome (or any other previously loaded biological sequence) of interest, and then to begin selecting individual genotype samples to be displayed on this chromosome. As each individual sample is selected, the genome browser begins loading the compressed low-resolution tiles for this genotype sample over the network, without blocking further user input, then decompresses them and renders a preview on the screen. When the user selects all of the samples of interest, the display generally begins with a representation of their full-length continuous sequence on the screen. At such low magnification, every pixel may contain a representation of thousands of base-pairs, and thus the sampled data is sufficient to render a zoom-appropriate view. As the user zooms in closer, the genome browser begins loading and decompressing high-resolution tiles in the background. In some implementations (e.g., where network latency is sufficiently low), these tiles can beneficially be fully loaded and decompressed by the time the user increases magnification to the point where individual base-pairs become discernible. When the user changes his viewport, e.g. by scrolling and/or zooming in and out, or a combination of both, the decompressed data for tiles that are no longer visible on screen is discarded, but their compressed representations are retained in memory. Doing so provides for a much faster user experience when scrolling (or when zooming in and out in order to alternate between a few points of interest on the chromosome), without sacrificing too much of the available RAM.

To speed up response times for displaying very large numbers of data points, e.g. millions, the genome browser may use a subset of the data. For example, the set of SNPs for one individual sample for one chromosome can contain several millions of SNPs while a screen may allow drawing of only about one thousand distinguishable lines. Consequently, a reasonable graphical representation of the whole data set can be accomplished with a thousand-fold reduction in data points. The genotype samples can be ordered by genetic distance to a reference genotype. This distance is based on comparing SNPs at identical positions. Deriving a reduced set in a naive way may lessen the chance to find sampled SNPs at identical positions for the genotypes to be displayed and may require relatively significant processing time. To solve this problem, the genome browser can in some implementations select the SNPs at identical positions for use in comparisons in such a way that maximizes probability to find a SNP at the precise same positions in different samples. This may be done by marking chromosome coordinate with "key-frame" nucleotide positions and selecting for comparison only SNPs in their vicinity. This procedure can greatly increase the chance of finding corresponding SNPs at the same coordinate during comparison of the selected genotypes, and can greatly reduce the processing time for producing the representation to be displayed.

Figure 2:
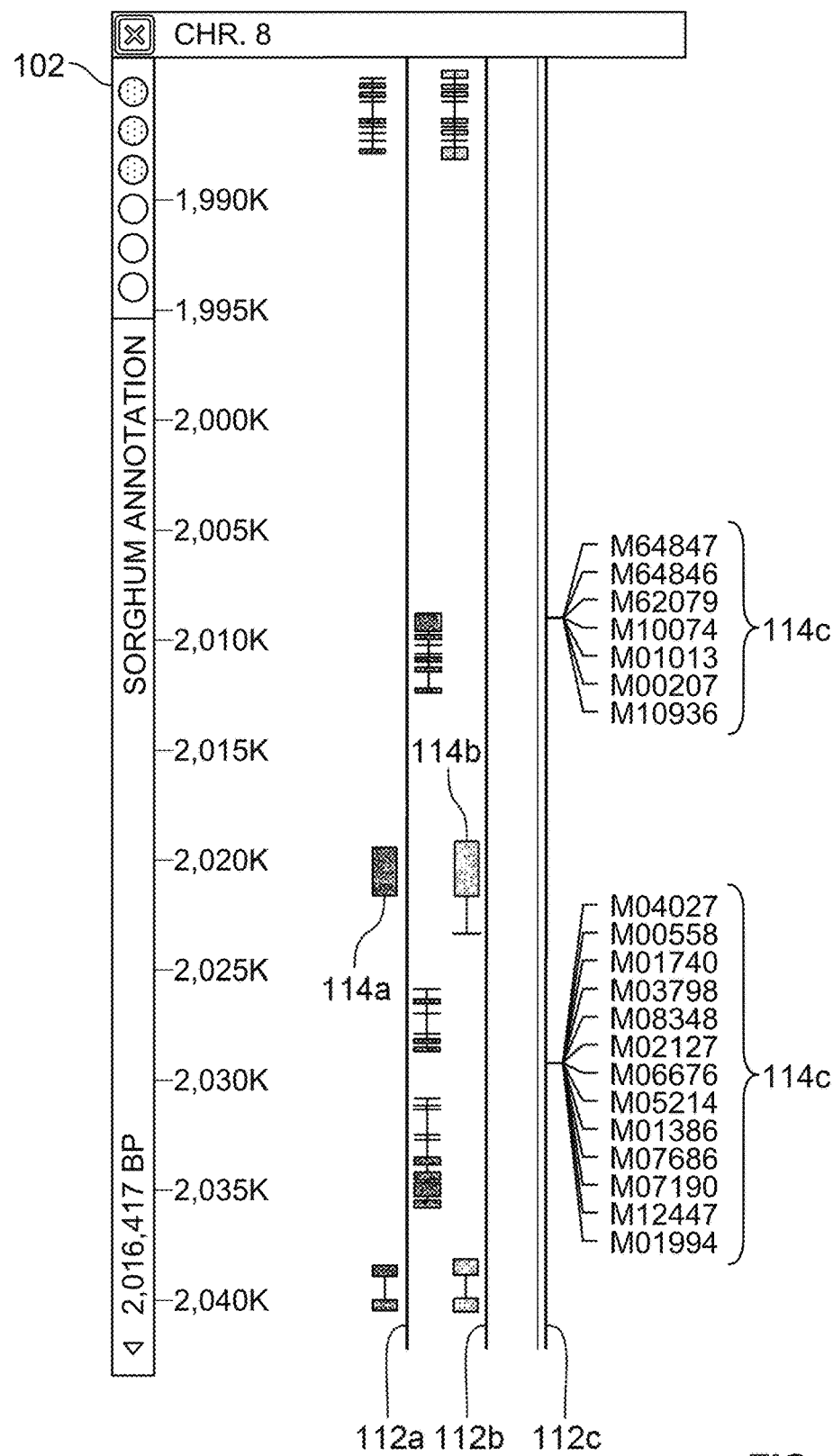
FIG. 2 depicts a browsing plate window zoomed-in to a region of a *Sorghum* chromosome, the browsing plate showing three vertical tracks indicating the locations of codons, mRNAs, and single nucleotide polymorphisms in the zoomed chromosomal region.

As mentioned above, the browser plate 102 may be zoomed to view segments of a sequence in greater detail and/or with greater resolution. FIG. 2, for example, depicts a browsing plate component 102 (here, a window of the user interface 100) zoomed-in to a region of the *Sorghum* chromosome that was shown in whole in FIG. 1. The zoomed browsing plate 102 shown in FIG. 2 shows three features of selected *Sorghum* organism along three respective genotype tracks 112a-c around the 2M (2000K) mark of the scale 100. As can be seen from FIG. 2, the features on each track 112a-c are shown with much greater resolution in the zoomed view. The user can identify locations, relative size, and spacing of the features with greater precision in the zoomed view. For example, the first track 112a shows graphical elements 114a for codons at corresponding locations along the chromosome sequence; the second track 112b shows graphical elements 114b for mRNAs at corresponding locations along the chromosome sequence; and the third track 112c shows graphical elements 114c for polymorphisms (SNPs) at corresponding locations along the chromosome sequence. Moreover, in the zoomed-in view, more detailed information can also be populated and shown in browser plate 102. From the zoom level shown in FIG. 2, the user may zoom out again to see all or a greater portion of the sequence, or may zoom in further for even closer inspection of a smaller portion of the sequence. The user may also scroll to different portions of the sequence within a particular zoom level in some implementations.

Figure 3:
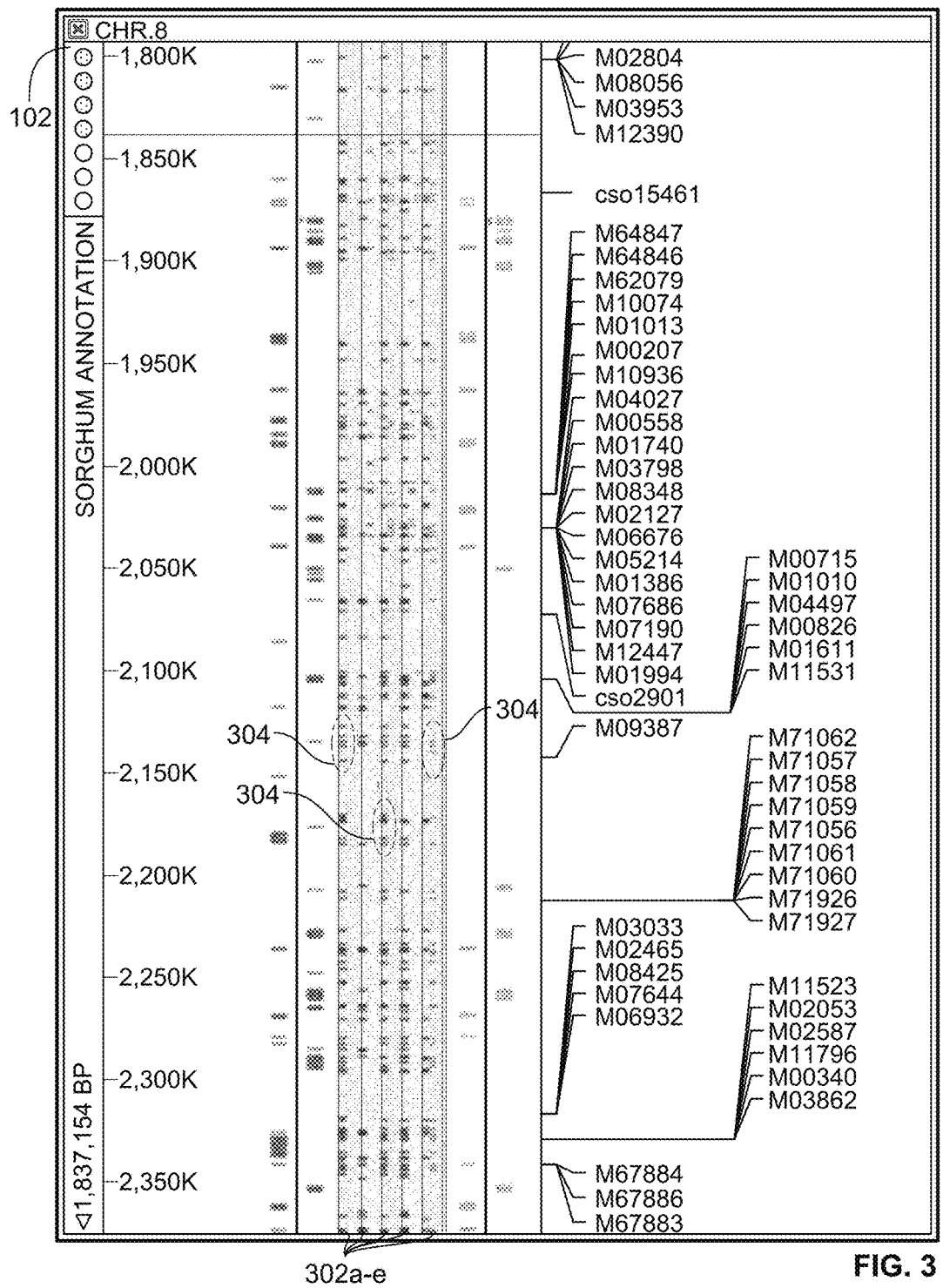
FIG. 3 depicts a browsing plate window zoomed-in to a region of the *Sorghum* chromosome that shows respective vertical tracks of genomic data for five different genotyped *Sorghum* samples.

FIG. 3 depicts a browsing plate window 102 zoomed-in to a region of the *Sorghum* chromosome that shows respective vertical tracks of genomic data for five different genotyped *Sorghum* samples. The genotypes for each sample are shown in the five parallel tracks 302a-e within the browsing plate 102. In this way, the genome browser is capable of displaying representations of the genotype, or representations of other genomic-related features, in parallel within a single browsing plate 102. Similarities and differences can then be identified at particular locations. For example, the browsing plate 102 shown in FIG. 3 is again zoomed-in to near the 2M (2000K) mark of the base-pair scale 110.

In some implementations, when genome features for more than one organism are selected for display, one, two, or more of the organisms can be designated as reference organisms. Tracks for the reference organisms can be displayed in positions within the browsing plate 102 that are reserved for the reference organisms. For example, the reference organisms may be displayed left-most within a group of tracks showing a particular feature in the browsing window 102. FIG. 3 shows that a first one of the genotyped *Sorghum* samples is shown in the left-most position within the group of five tracks 302a-e (i.e., track 302a shows the representation of the genotype for the reference organism). In some implementations, any of a group of organisms may be designated as a reference organism without regard to the position of the designated organism's track in the browsing window 102. In some implementations, multiple reference organisms may be designated. For example, a user may select (or a computing system may automatically select according to pre-defined criteria) a pair of organisms that are the parents, or that have another type of ancestral relationship, to the other organisms that have been selected for display. In this way, genomic data of ancestral samples can be analyzed concurrently with samples of the ancestor's progeny. This can be useful for analyzing two reference individuals who are inbred parents, and their segregating progeny populations. For qualitative traits, it can be useful to align the genotypes of parents with those of children who might or might not be affected by the qualitative trait.

In some implementations, designating a reference organism can allow a user to compare one or more individuals (organisms) with a phenotype of interest to controls, as phenotype-linked polymorphisms may be noticeable by their different colors. When a reference individual is changed, its genetic similarity of the other individuals to be displayed can be calculated based on available polymorphisms, and the individuals can be re-ordered so as to maximize the similarity of adjacent genotype tracks.

As a result of designating certain organisms as references, the computing system can compare the features of the other, non-designated organisms, to the features of the designated organisms. The features of the respective tracks 302b-e of the non-designated organisms can be displayed in the browsing plate 102 relative to the corresponding features of the designated organisms. For example, as shown in FIG. 3, the respective tracks 302b-e for the non-designated Sorghum samples represent particular features of those samples relative to the corresponding features of the designated reference organism whose features are represented by track 302a. In particular, SNPs of the reference organism are represented by bands 304a along the first track 302a. Where corresponding SNPs are genotyped in the non-designated organisms, bands 304b-e are shown along the respective tracks 302b-e. Differences between features of the reference organism and the others can be graphically represented by distinctive aspects of the bands 304. For example, the polymorphisms in the reference organism can be shown by bands 304a that are shaded in a first color (e.g., blue), whereas opposite corresponding polymorphisms in the other organisms can be shown by bands 304b-e that are shaded in a second color (e.g., red).

In some implementations, the designation of the reference organism or organisms can change, and tracks 304a-e can be re-ordered within the browsing plate 102. A user can manually re-arrange the tracks, such as by selecting one or more tracks and dragging them to different locations within the browsing plate 102. In some implementations, the user may designate a new organism as a reference organism, and the tracks can be automatically re-ordered in response to the new designation. For example, the user may select the third track 302c to designate the organism corresponding to the third track 302c as the reference organism. Once the new designation is effected, track 302c may be automatically moved to the left-most position (where track 302a was previously positioned). The features of the non-designated organisms can then be re-compared with the newly designated reference organism, and the displays adjusted so that the elements (e.g., bands) along the tracks 302 are shown as having some relationship to the new reference organism rather than (or in addition to, if multiple reference organisms are designated) to the previous reference organism.

Further, the tracks 302b-e corresponding to the non-designated organisms can be automatically or manually re-ordered. For example, the computing system may compare the genotype of the reference organism to each of the other non-designated organisms and determine a similarity score for each of the non-designated organisms that indicates how similar its genotype is to the genotype of the reference organism. The tracks can then be re-ordered automatically so that the track of the organism whose genotype is most similar to that of the reference organism is displayed adjacent or otherwise nearest to the track of the reference organism, and the remaining tracks ordered according to descending similarity. In some implementations, the similarity scores among genotypes (or other specific genome-related data such as expression levels, polymorphisms, QTLs, etc.) can be calculated based on comparisons of substantially the entire genotypes of the organisms. In some implementations, the similarity scores among genotype (or other genome-related data) can be calculated based on comparisons of only a portion of the genotypes of the organisms, such as only the portion that is being displayed (e.g., around the 2000K portion for the example depicted in FIG. 3). A user may also enter the range of the chromosome sequence that should be compared for the purpose of determining similarities among the genotypes.

Figure 4:
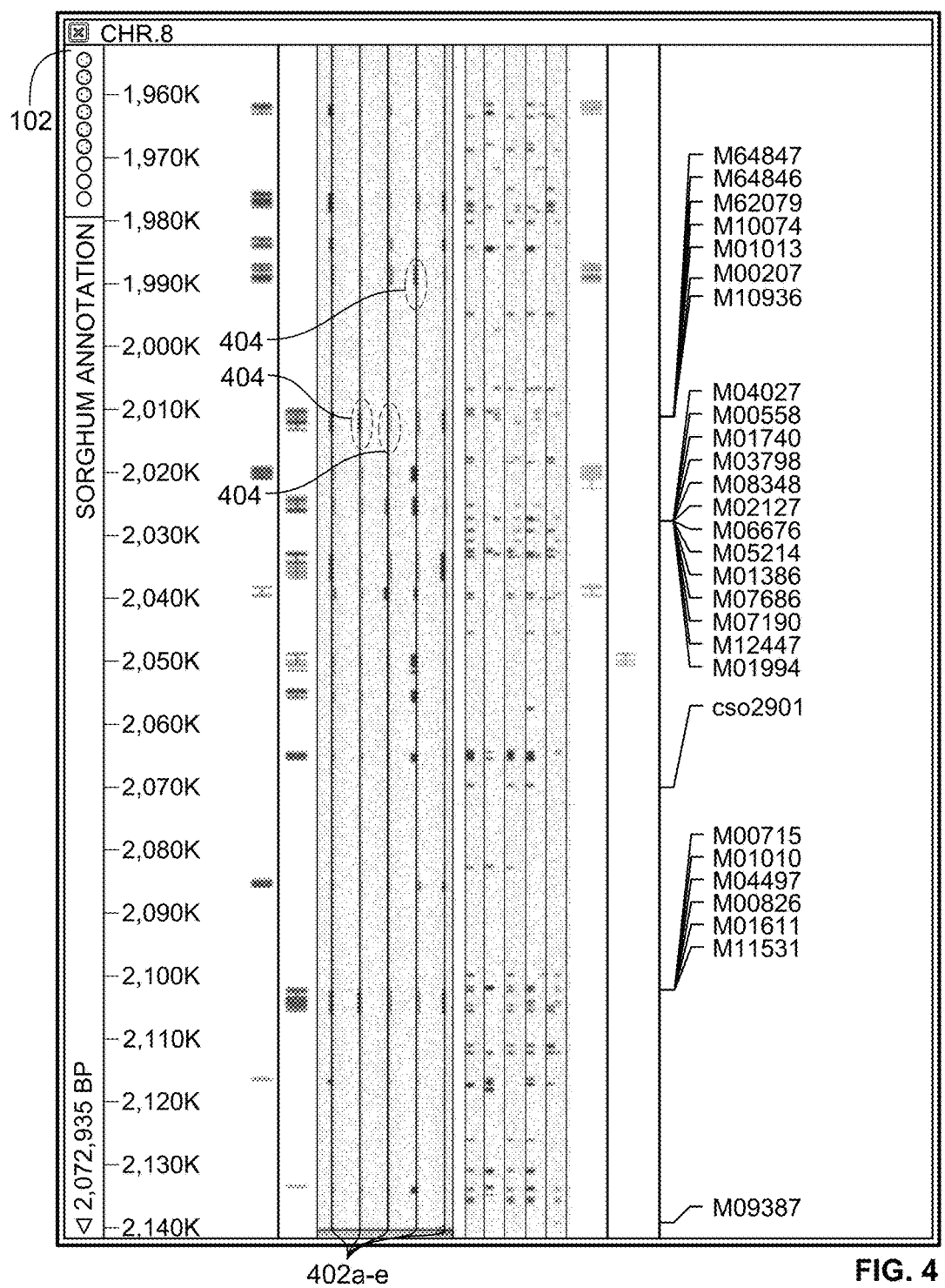
FIG. 4 depicts a browsing plate window zoomed-in to a region of the *Sorghum* chromosome that shows respective vertical tracks depicting expression levels of genes at corresponding locations of the chromosomal sequence for five different *Sorghum* tissue samples.

FIG. 4 depicts a window of a browsing plate 102 zoomed-in to a region of the Sorghum chromosome in which a plurality of tracks 402a-e have been added that include representations of gene expression levels at corresponding locations of the chromosomal sequence for five different Sorghum tissue samples. The gene expression levels may be obtained from map data or other data associated with the particular chromosome of the subject organism (e.g., Sorghum chromosome 8). The expression level tracks 402a-e may be added to the same browsing plate 102 window as genotype tracks that show locations of codons, mRNAs, and SNPs in some implementations, so that a user may readily compare the expression levels and genotypes among multiple organisms.

In some implementations, the representations of expression levels on tracks 402a-e can follow the reference organism model described above with respect to FIG. 3. The expression levels of non-reference organisms or tissue expression samples can be compared to corresponding expression levels of the designated reference organism or tissue expression sample. Based on such comparison, the expression level markers 404 (bands) along tracks 402a-e may visually indicate the expression levels relative to the expression levels of corresponding genes in the reference. For example, a user may designate a first Sorghum sample as the reference organism, so that its expression levels 404a are shown along the first track 402a on the left. The expression levels for each of the non-designated samples can be shown along the other tracks 402b-e relative to the expression levels in the first track. The markers 404 along the tracks can be formatted in a manner that visually indicates relative expression levels. For example, the markers 404 can comprise colored bands in which the band color indicates overexpression or underexpression relative to expression level of the corresponding gene in the reference level (e.g., blue band indicates overexpression, red band indicates underexpression). The width of the band can be made proportional to the magnitude of difference from a mean expression level or from a corresponding expression level of a gene in the reference organism.

In some implementations, additional expression tracks may be added to the window of the browser plate 102 that show expression levels exhibited by individuals or tissues in different conditions. For example, the browser plate 102 may show a track indicating the genotype of a particular organism, as well as multiple expression level tracks that show expression levels of genes for the particular organism in which different levels of drugs have been administered.

In some implementations, the browser plate 102 may show multiple polymorphisms at the same point in the genotype track for heterozygous individuals. Occurrences of multiple polymorphisms at the same point may be graphically shown with a split, multi-colored band in the genotype track (e.g., a split red-blue band). Corresponding allele-specific expression levels for a heterozygous individual can also be visually presented in a manner that indicates the allele-specific expression levels, such as by shading the bands according to the relative expression levels among each allele.

In some implementations, tracks may be added to the browser plate 102 that identify the locations of quantitative trait loci (QTLs). QTL markers along the tracks can pinpoint locations of QTLS that have been found to be significant in one or more studies. Representations of logarithm of odds (LOD) scores from genome-wide association studies (GWAS studies) may also be marked at respective locations along the tracks. In some implementations, the browser plate 102 may indicate the locations of CpG islands by placing markers that indicate CpG islands along one or more tracks at corresponding sequence locations.

Figure 5:
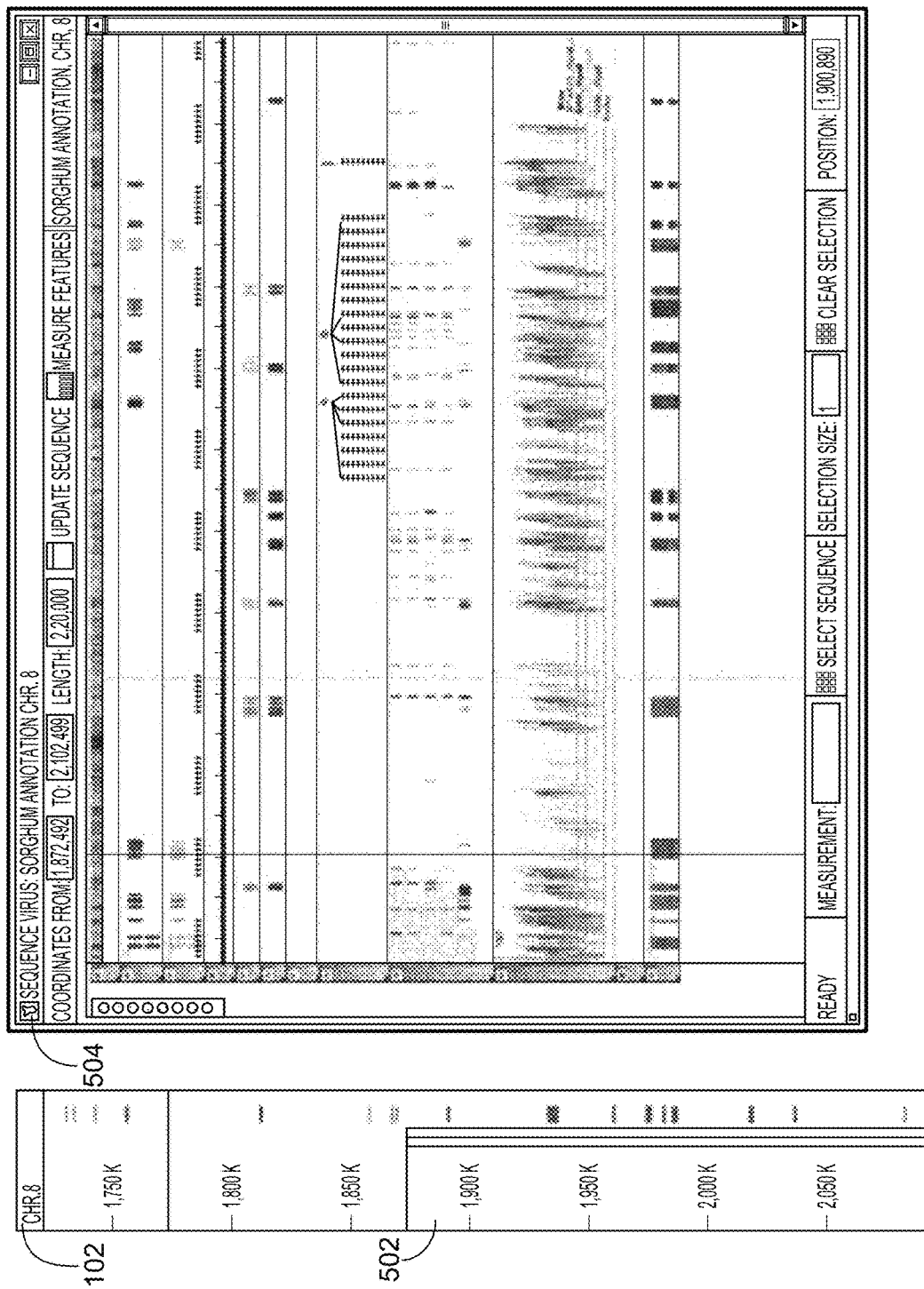
FIG. 5 depicts a particular region of the *Sorghum* chromosome that a user has selected for display in a separate window of the genome browser showing a detailed representation of genomic and related data for the *Sorghum* chromosome over the selected region for five different *Sorghum* tissue samples.

FIG. 5 illustrates a user's selection of a particular region 502 of the Sorghum chromosome, and a corresponding browser window 504 that the computing system launches based on the selected region 502. A user may drag along the scale 110 in the browser plate 102 to select a particular region of the chromosome for closer inspection. In response, the computing system can cause detailed information to be displayed in the browser plate 102 or in a separate display region or window 504. The information may be displayed in a suitable way, such as along vertical or horizontal tracks. A user may desire to inspect a region of a chromosome closer, for example, if it seems to have conserved haplotypes between recombination hot spots. In some implementations, it is feasible to select different reference individuals and to re-arrange the group displayed by genetic distance of the selected region.

Figure 6:
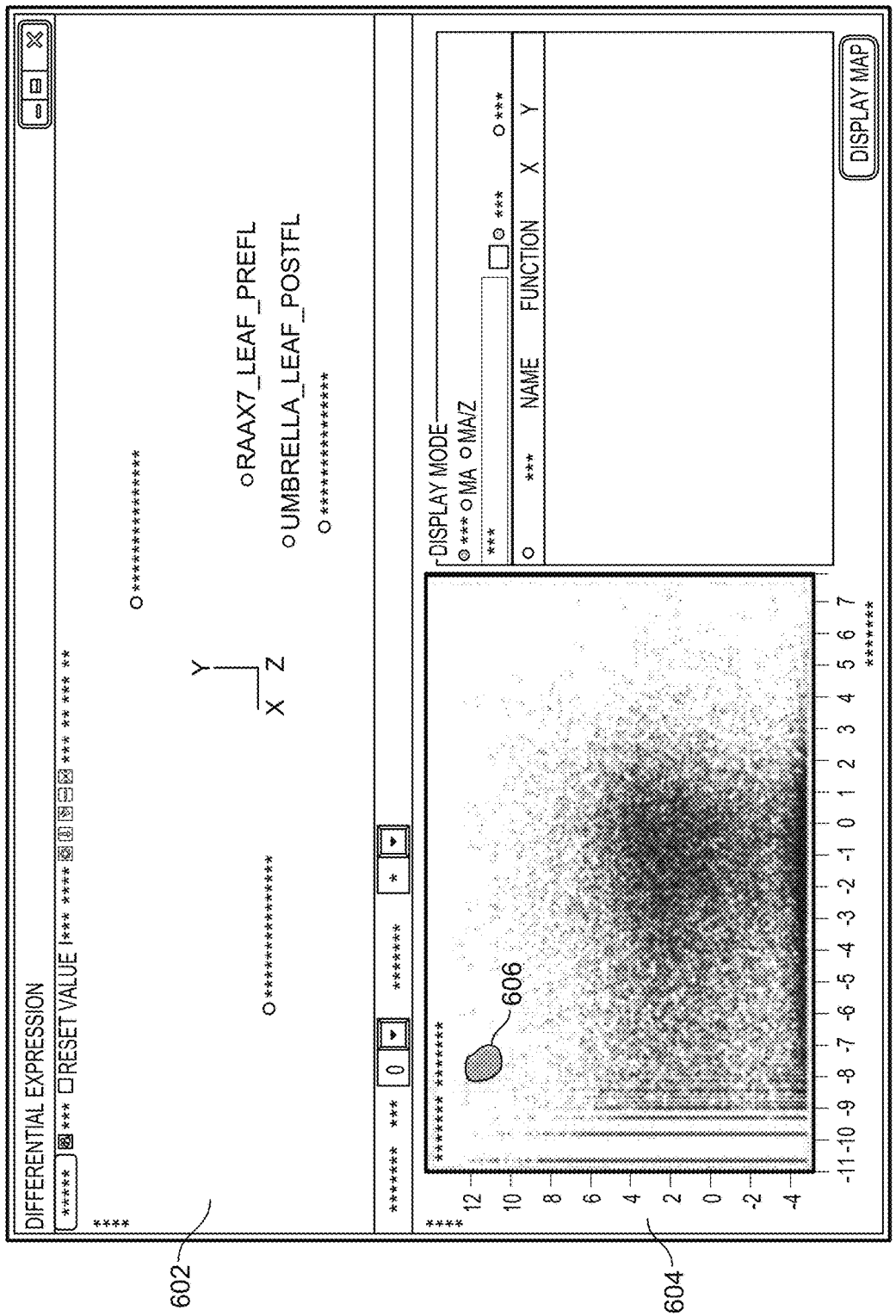
FIG. 6 depicts a multidimensional scaling (MDS) plot of gene expression levels for the five *Sorghum* samples, and a scatter plot of the gene expression levels for the five *Sorghum* tissue samples.

FIG. 6 depicts two plots that show different representations of gene expression levels for the five different Sorghum samples. In some implementations, in addition to displaying selected expression data for multiple organisms aligned in the chromosome browser plate 102, the computing system can generate and display one or more plots of the data. At top of FIG. 6 is shown a multi-dimensional scaling (MDS) plot of selected expression data for multiple organisms. Additionally, the represented individuals can be assigned to different groups, and their differentially expressed genes displayed in a scatter plot, as shown at the bottom of FIG. 6. Genes with the greatest differences in expression can be easily seen from the plots, selected (see shaded selection 606), and identified. Moreover, the computing system may allow the user to perform similar techniques of plotting, selection, and identification on limited-length haplotypes.

Figure 7:
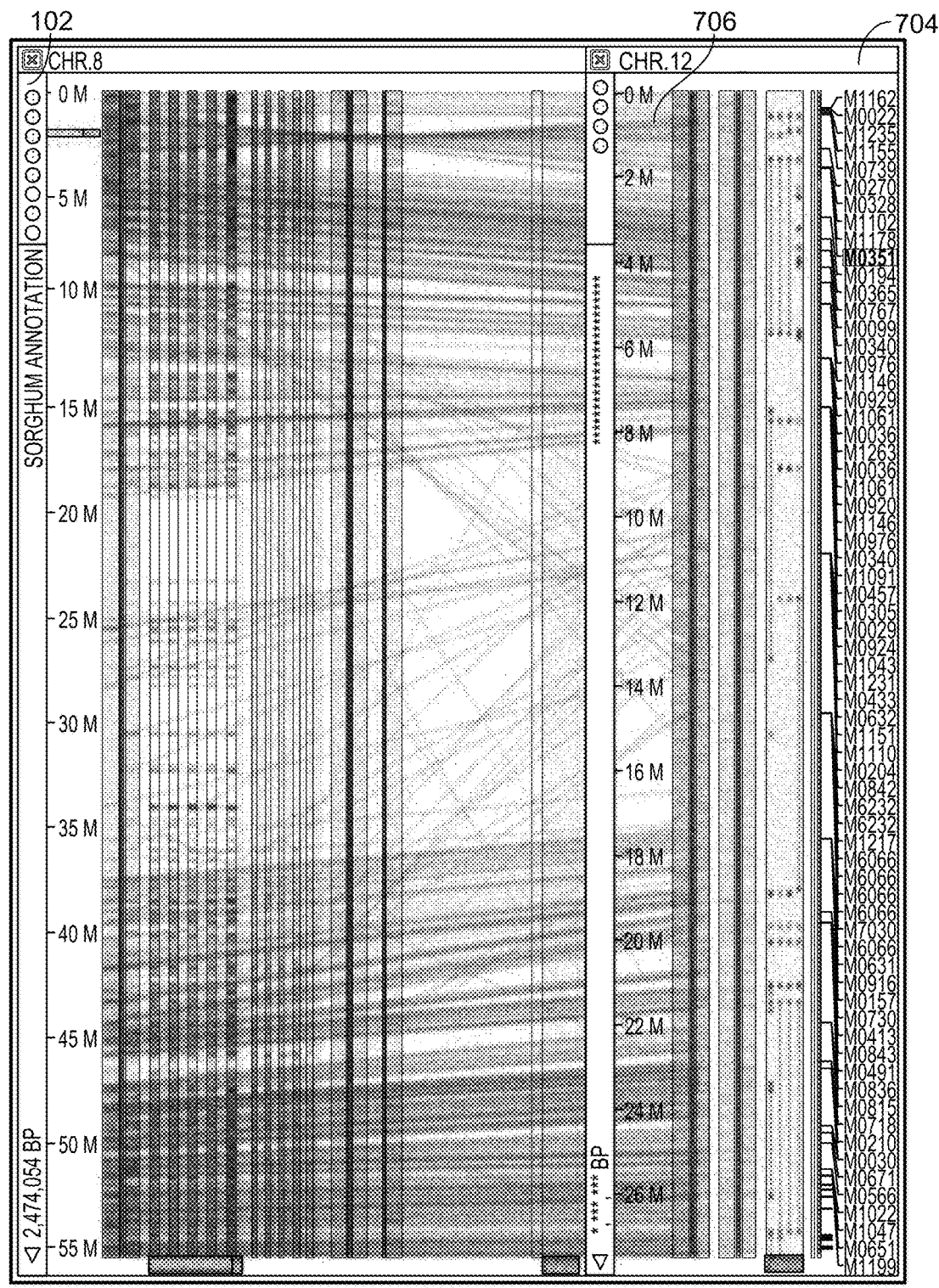
FIG. 7 depicts the simultaneous display of a first browser plate for a *Sorghum* chromosome and a second browser plate for a rice chromosome, along with connecting lines that indicate syntenic regions between the *Sorghum* and rice chromosomes.
Figure 8:
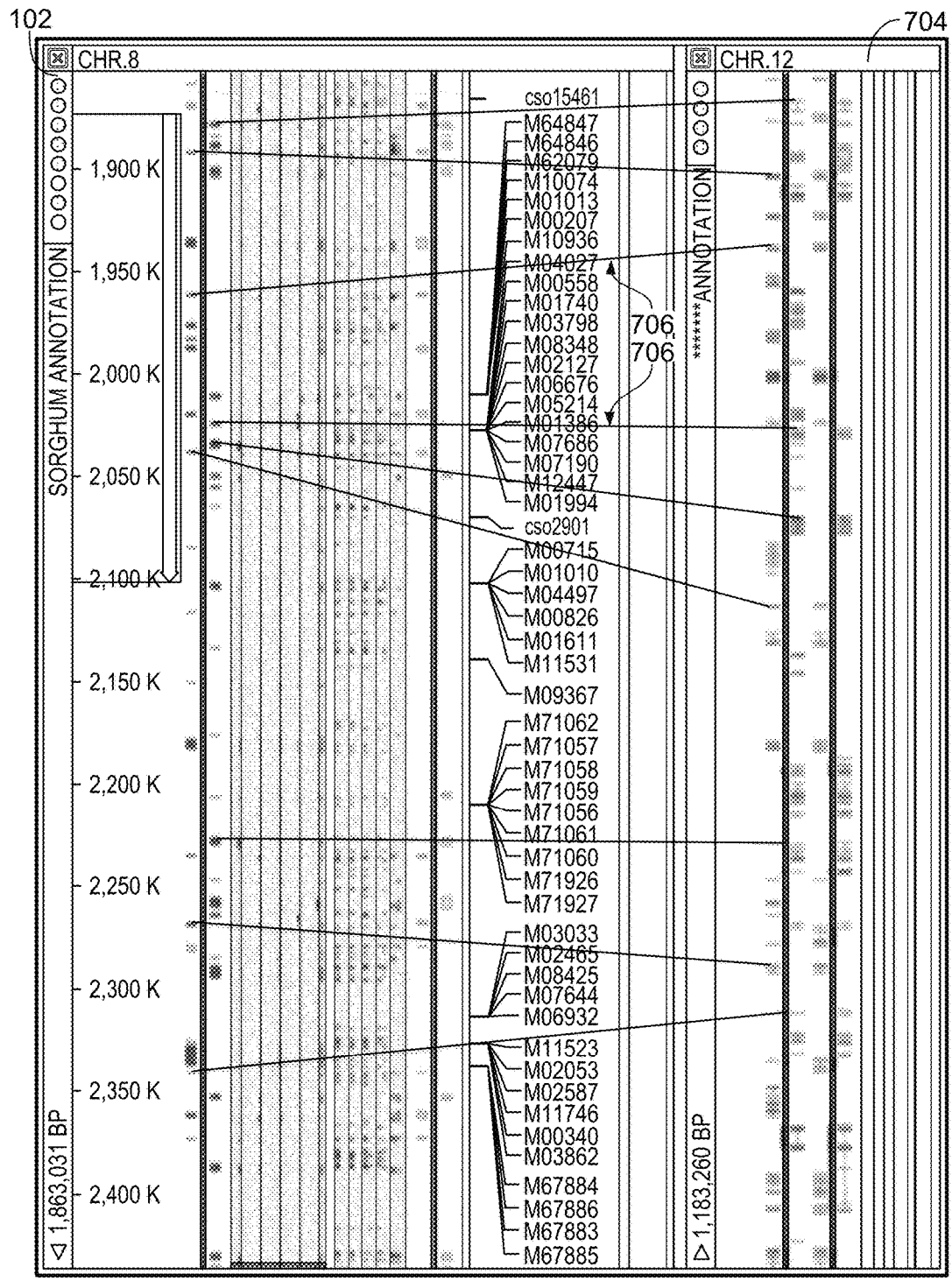
FIG. 8 depicts the first and second browser plates for the *Sorghum* and rice chromosomes of FIG. 7, respectively, zoomed-in to a display of a smaller region of the chromosomes.

FIGS. 7 and 8 each depict a pair of browser plates 102, 704 for chromosomes of different organisms, along with connecting lines 706 that indicate syntenic regions between the chromosomal sequences of the organisms. In some implementations, a genome browser can simultaneously display two different chromosomes and indicate syntenic regions. Synteny of chromosomes of different species can be determined by finding similarly ordered homologous coding sequences. FIG. 7 shows the syntenic relationship of the entire Sorghum chromosome 8 and rice chromosome 12. FIG. 8 shows a zoomed-in view on a smaller region of the respective sorghum and rice chromosomes. The rice chromosome is annotated with genes and QTLs. A user can look, for example, into whether or not similar QTLs are associated with a region of interest, and whether or not the homologous genes are involved. The sorghum chromosome is represented in browser plate 102, and the rice chromosome is represented in browser plate 704. The computing system can determine syntenic regions and draw connecting lines 706 that connect between the syntenic regions of the selected chromosomes.

Figure 9:
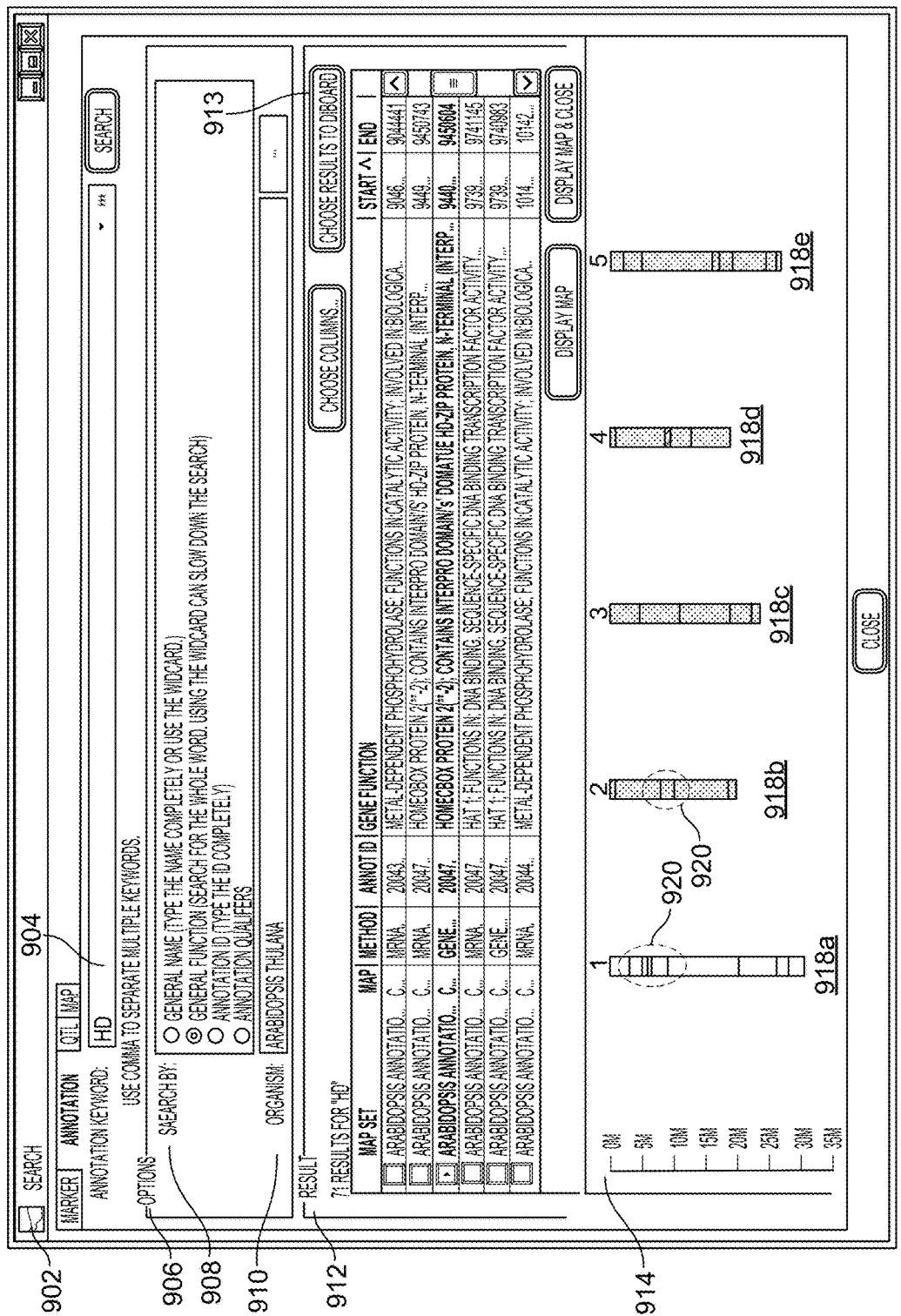
FIG. 9 depicts a search function of the genome browser in which a search is performed for a gene function in chromosomes of *Arabidopsis thaliana* and results are shown first in tabular form and second graphically at corresponding locations of the *Arabidopsis thaliana* chromosomes.

FIG. 9 depicts an example search function of the genome browser. The search function may be accessed from the user interface 100 of the genome browser, and can facilitate efficient lookup of particular data of interest. The user may search for various information within genome-related data for one or more organisms. For example, a user may search for different genes, gene functions, nucleotide sequences, expressions, alleles, and more. As shown in FIG. 9, a user has entered the query "HD" in the Annotation Keyword field to perform a search. In some implementations, the genome-related data for particular organisms that is accessible to the computing system may be annotated with keywords or other data, such as gene names, or gene functions. The annotations, and other searchable information, may be associated with particular locations or regions of a sequence (e.g., of a chromosomal sequence). Accordingly, when the computing system returns results that are determined to be responsive to the search query, all or some of the search results may indicate particular locations or regions of a sequence of interest. For example, FIG. 9 shows a number of search results that indicate sequence locations in various chromosomes for Arabidopsis thaliana, which are graphically shown at corresponding locations of linear representations 918a-e of the chromosomes in results box 914.

The computing system can provide a search options box 906 that allows a user to select one or more parameters for the search. In some implementations, the user can specify a "search by" parameter that indicates different fields or features for the search. The search may be performed by Gene Name, Gene Function, Annotation ID, or Annotation Qualifiers, for example; or it may be performed by sequence similarity searches, such as BLAST searches. In some implementations, the search may be performed by multiple fields or features (e.g., the user may select a combination of one or more of the Gene Name, Gene Function, Annotation ID, and Annotation qualifiers). A default selection may be made by the computing system in this regard as well. Additionally, the user may specify a particular organism to be associated with the search, so that the search is configured to locate results associated with only the specified organism. In some implementations, the user may specify multiple organisms for the search. The organism may be specified by species name in some implementations, which is shown in FIG. 9, where the user has identified Arabidopsis thaliana for the search.

After the user submits the query and the computing system identifies search results responsive to the query, the search results can be presented. In some implementations, a list of search results can be presented in tabular form. For example, results box 912 shows 71 search results returned for the user's "HD" gene function search. The results box 912 includes a respective row for each search result, along with various columns that indicate information about the search results. Results box 912 includes columns that indicate which map set and particular map that the result was obtained from, an annotation ID, a gene function description, and start and end sequence locations of the chromosome that corresponds to the result. The user may configure which columns are to be displayed in the results box 912, and may add or remove columns as desired. The columns may also be re-arranged into a different order. The results box 912 can also include a control 913 that allows a user to copy one or more selected results into a clipboard, so that a summary of the selected results or the information underlying the results can be pasted into a separate file or application.

In some implementations, a graphical representation of the search results can be provided. FIG. 9 includes a second results box 914 that shows linear representations 918a-e of five Arabidopsis thaliana chromosomes. The search results are represented by sequence markers 920 (bands), which are displayed at locations over the linear representations 918a-e of the chromosomes that correspond to the sequence locations indicated by the search results. The graphical representation of search results in this manner may more readily allow the user to see and understand the context of the search results. Any of the sequence markers 920 may be selected (e.g., by a mouse-click or tap on a touchscreen) to view the corresponding search result for the selected marker 920 in greater detail. In some implementations, a sequence marker 920 can be selected to cause a browser plate 102 to launch in a separate window that shows a representation of genome-related data for the organism whose search result was selected. The browser plate 102 can be automatically scaled to show only a particular region of a chromosome at or around the locations indicated by the selected search result. Similarly, search results may be selected from the list in results box 912 so as to launch a browser plate 102 window showing representations of data corresponding to the selected search result.

Figure 10:
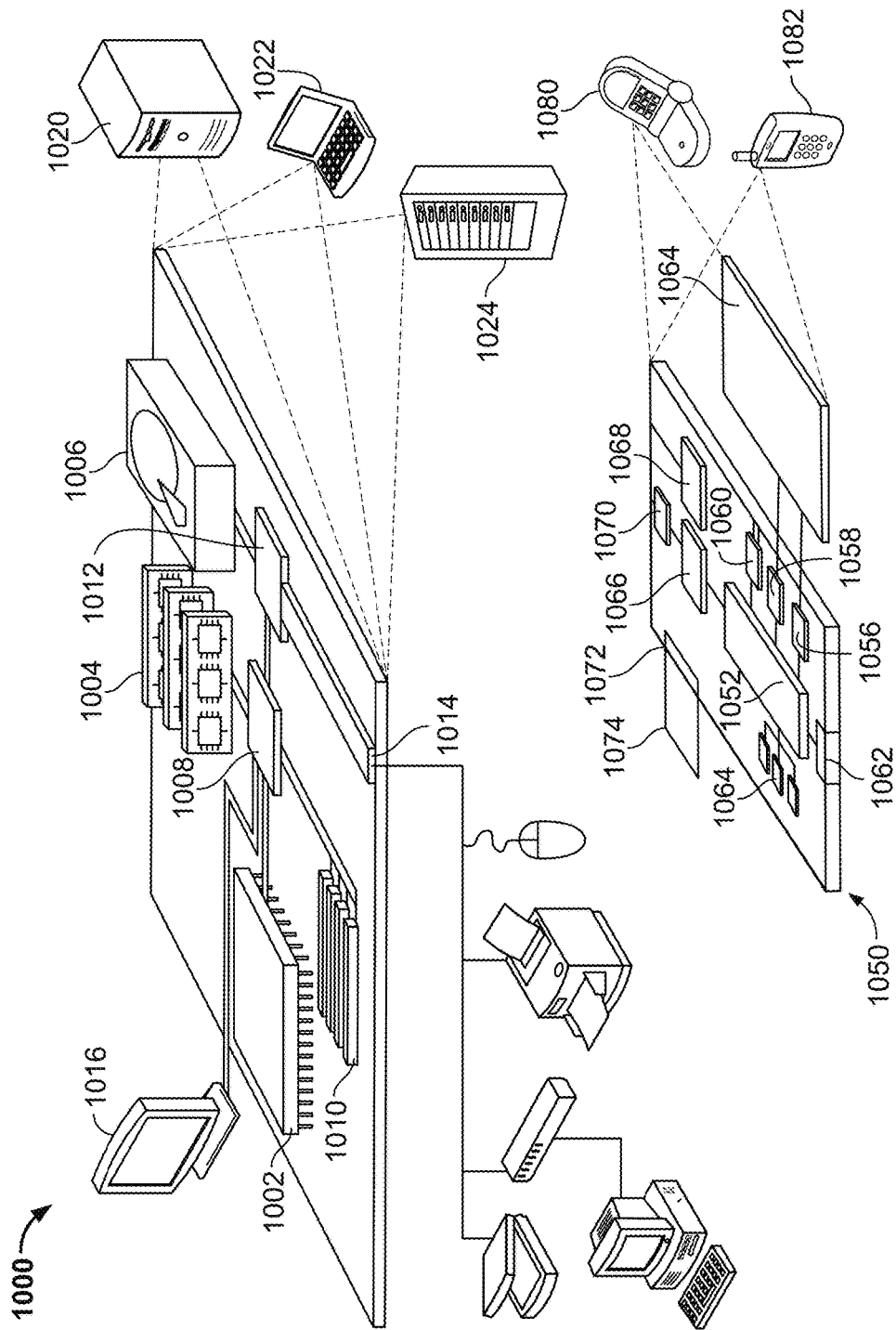
FIG. 10 depicts an example of a computing device and a mobile computing device that can be used to implement the systems, methods, and other techniques described herein.

FIG. 10 shows an example of a computing device 1000 and a mobile computing device that can be used to implement the techniques described herein. The computing device 1000 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1004 stores information within the computing device 1000. In some implementations, the memory 1004 is a volatile memory unit or units. In some implementations, the memory 1004 is a non-volatile memory unit or units. The memory 1004 may also be another form of computer-readable medium, such as a magnetic or optical disk.

The storage device 1006 is capable of providing mass storage for the computing device 1000. In some implementations, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. The computer program product may also contain instructions that, when executed, perform one or more methods, such as those described above. The computer program product can also be tangibly embodied in a computer- or machine-readable medium, such as the memory 1004, the storage device 1006, or memory on the processor 1002.

The high-speed interface 1008 manages bandwidth-intensive operations for the computing device 1000, while the low-speed interface 1012 manages lower bandwidth-intensive operations. Such allocation of functions is exemplary only. In some implementations, the high-speed interface 1008 is coupled to the memory 1004, the display 1016 (e.g., through a graphics processor or accelerator), and to the high-speed expansion ports 1010, which may accept various expansion cards (not shown). In the implementation, the low-speed interface 1012 is coupled to the storage device 1006 and the low-speed expansion port 1014. The low-speed expansion port 1014, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. In addition, it may be implemented in a personal computer such as a laptop computer 1022. It may also be implemented as part of a rack server system 1024. Alternatively, components from the computing device 1000 may be combined with other components in a mobile device (not shown), such as a mobile computing device 1050. Each of such devices may contain one or more of the computing device 1000 and the mobile computing device 1050, and an entire system may be made up of multiple computing devices communicating with each other.

The mobile computing device 1050 includes a processor 1052, a memory 1064, an input/output device such as a display (not shown), a communication interface 1066, and a transceiver 1068, among other components. The mobile computing device 1050 may also be provided with a storage device, such as a micro-drive or other device, to provide additional storage. Each of the processor 1052, the memory 1064, the display 1054, the communication interface 1066, and the transceiver 1068, are interconnected using various buses, and several of the components may be mounted on a common motherboard or in other manners as appropriate.

The processor 1052 can execute instructions within the mobile computing device 1050, including instructions stored in the memory 1064. The processor 1052 may be implemented as a chipset of chips that include separate and multiple analog and digital processors. The processor 1052 may provide, for example, for coordination of the other components of the mobile computing device 1050, such as control of user interfaces, applications run by the mobile computing device 1050, and wireless communication by the mobile computing device 1050.

The processor 1052 may communicate with a user through a control interface 1058 and a display interface 1056 coupled to the display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may provide communication with the processor 1052, so as to enable near area communication of the mobile computing device 1050 with other devices. The external interface 1062 may provide, for example, for wired communication in some implementations, or for wireless communication in other implementations, and multiple interfaces may also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 may also be provided and connected to the mobile computing device 1050 through an expansion interface 1072, which may include, for example, a SIMM (Single In Line Memory Module) card interface. The expansion memory 1074 may provide extra storage space for the mobile computing device 1050, or may also store applications or other information for the mobile computing device 1050. Specifically, the expansion memory 1074 may include instructions to carry out or supplement the processes described above, and may include secure information also. Thus, for example, the expansion memory 1074 may be provide as a security module for the mobile computing device 1050, and may be programmed with instructions that permit secure use of the mobile computing device 1050. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. The computer program product contains instructions that, when executed, perform one or more methods, such as those described above. The computer program product can be a computer- or machine-readable medium, such as the memory 1064, the expansion memory 1074, or memory on the processor 1052. In some implementations, the computer program product can be received in a propagated signal, for example, over the transceiver 1068 or the external interface 1062.

The mobile computing device 1050 may communicate wirelessly through the communication interface 1066, which may include digital signal processing circuitry where necessary. The communication interface 1066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1068 using a radio-frequency. In addition, short-range communication may occur, such as using a Bluetooth, WiFi, or other such transceiver (not shown). In addition, a GPS (Global Positioning System) receiver module 1070 may provide additional navigation- and location-related wireless data to the mobile computing device 1050, which may be used as appropriate by applications running on the mobile computing device 1050.

The mobile computing device 1050 may also communicate audibly using an audio codec 1060, which may receive spoken information from a user and convert it to usable digital information. The audio codec 1060 may likewise generate audible sound for a user, such as through a speaker, e.g., in a handset of the mobile computing device 1050. Such sound may include sound from voice telephone calls, may include recorded sound (e.g., voice messages, music files, etc.) and may also include sound generated by applications operating on the mobile computing device 1050.

The mobile computing device 1050 may be implemented in a number of different forms, as shown in the figure. For example, it may be implemented as a cellular telephone 1080. It may also be implemented as part of a smart-phone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Although various implementations have been described in detail above, other modifications are possible. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method for displaying and analyzing sequenced genome data, the method comprising:
   obtaining, by a computing system, genomic data for a plurality of organisms;
   generating, by the computing system and based at least on the genomic data for the plurality of organisms, a browser plate component displaying a first graphical representation of the genomic data, the first graphical representation comprising a plurality of vertical parallel tracks that are arranged to show one or more features of the genomic data for different ones of the plurality of organisms, wherein the plurality of vertical parallel tracks includes a first track that shows a first particular feature of a first organism, a second track that shows the first particular feature of a second organism, and a third track that shows the first particular feature of a third organism; and
   upon an identification, by the computing system, that the first organism is designated as a reference organism, reconfiguring, by the computing system and in response to identifying that the first organism is designated as the reference organism, the browser plate component to display a second graphical representation of the plurality of vertical parallel tracks in the second graphical representation of the genomic data so that the first track that shows the first particular feature of the first organism is shown in a reference position of the graphical representation, the second and third tracks are shown in respective positions proximate to the reference position, and the first particular features of the second and third tracks are each shown relative to the first particular features of the first track, wherein reconfiguring the browser plate component comprises rearranging each vertical parallel track in accordance with a rank corresponding to a similarity score between each vertical parallel track and the first track.

2. The computer-implemented method of claim 1, wherein the graphical representation of the genomic data is a first graphical representation of genomic data of a first chromosome;
   the method further comprising generating, by the computing system, a second graphical representation of genomic data of a different, second chromosome, the second graphical representation comprising one or more tracks that are arranged to show one or more features of the genomic data of the second chromosome for at least one organism; and
   outputting the second graphical representation for display.

3. The computer-implemented method of claim 2, further comprising determining, by the computing system, syntenic regions of the genomic data of the first chromosome and the genomic data of the second chromosome; and
   outputting, by the computing system, for display graphical elements that connect the first graphical representation and the second graphical representation, and that show corresponding syntenic regions of the genomic data of the first chromosome and the genomic data of the second chromosome.

4. The computer-implemented method of claim 1, further comprising identifying that user input has entered a search query associated with a particular organism; and
   obtaining, by the computing system, a set of search results that are determined to be responsive to the search query, each search result in the set of search results indicating a respective chromosomal sequence location for the particular organism.

5. The computer-implemented method of claim 4, further comprising generating and outputting for display, by the computing system, a graphical representation of one or more chromosomes for the particular organism that shows graphical markers at locations of the one or more chromosomes that correspond to the respective chromosomal sequence locations indicated by the set of search results.

6. The computer-implemented method of claim 4, further comprising receiving, by the computing system, an indication that user input selected a first search result from among the set of search results, and in response, automatically generating and outputting for display a graphical representation of the genomic data for the particular organism that shows a zoomed-in region corresponding to the location of the chromosome indicated by the first search result.

7. The computer-implemented method of claim 1, further comprising:
   receiving, by the computing system, an indication that the designation of the reference organism is changed from the first organism to the second organism; and
   in response to receiving the indication that the designation of the reference organism is changed:
   re-ordering, by the computing system, the plurality of tracks in the graphical representation of the genomic data so that the second track that shows the first particular feature of the second organism is shown in the reference position of the graphical representation, the first and third tracks are shown in respective positions outside of the reference position, and the first particular features of the first and third tracks are each shown relative to the first particular features of the second track, and
   outputting, by the computing system, the re-ordered graphical representation of the genomic data for display.

8. The computer-implemented method of claim 7, wherein re-ordering the plurality of tracks in the graphical representation comprises automatically arranging the plurality of tracks in descending order of determined genetic similarity between the second organism, due to the second organism being designated as the reference organism, and the corresponding organisms for each of the other tracks in the plurality of tracks, so that tracks corresponding to organisms that are more genetically similar to the second organism are caused to be shown in closer proximity to the second track and tracks corresponding to organisms that are less genetically similar to the second organism are caused to be shown a further distance from the second track.

9. The computer-implemented method of claim 7, further comprising determining, by the computing system, the genetic similarities between the second organism and the corresponding organisms for each of the other tracks in the plurality of tracks based only on data for a portion of the chromosomal sequence of the organisms currently being outputted for display.

10. The computer-implemented method of claim 1, wherein at least one of the plurality of tracks in the graphical representation shows a linear representation of codons in a chromosome sequence of an organism.

11. The computer-implemented method of claim 10, wherein at least one of the plurality of tracks is an mRNA track that shows locations of transcribed regions of the chromosome sequence.

12. The computer-implemented method of claim 1, wherein the first particular feature comprises single nucleotide polymorphisms (SNPs),
the method further comprising generating, by the computing system the graphical representation of the genomic data so that the second track shows, as a result of the first organism being designated as the reference organism, SNPs in the genomic data of the second organism relative to the genomic data of the first organism shown in the first track.

13. The computer-implemented method of claim 12, wherein the second track shows SNPs in the genomic data of the second organism relative to the genomic data of the first organism by showing colored elements along the second track at locations that correspond to locations in a chromosome sequence where SNPs occur that are opposite of SNPs in the genomic data of the first organism.

14. The computer-implemented method of claim 1, further comprising obtaining, by the computing system, data that indicates expression levels for corresponding portions of the genomic data for one or more of the plurality of organisms.

15. The computer-implemented method of claim 14, wherein the first particular feature comprises the expression levels for the corresponding portions of the genomic data,
the method further comprising generating, by the computing system, the graphical representation of the genomic data so that the second track shows, as a result of the first organism being designated as the reference organism, expression levels for the corresponding portions of the genomic data of the second organism relative to the expression levels of for the corresponding portions of the genomic data of the first organism.

16. The computer-implemented method of claim 15, wherein the second track shows allele-specific expression levels.

17. The computer-implemented method of claim 14, further comprising generating, by the computing system and based at least on the data that indicates the expression levels for the corresponding portions of the genomic data for the one or more of the plurality of organisms, a multidimensional plot showing variability in expression levels among different sets of expression data for particular ones of the plurality of organisms; and
outputting, by the computing system, the multidimensional plot for display.

18. The computer-implemented method of claim 17, wherein generating the multidimensional plot comprises automatically limiting the plot to showing only expression levels of sequences corresponding to a portion the genomic data being outputted for display in the graphical representation of the genomic data, to the exclusion of expression levels of sequences outside of the portion of the genomic data being outputted for display in the graphical representation of the genomic data.

19. The computer-implemented method of claim 1, wherein the first particular feature comprises at least one of quantitative trait loci (QTLs) and trait linkage scores for particular sequence locations.

20. The computer-implemented method of claim 1, wherein the first particular feature comprises CpG islands,
the method further comprising generating, by the computing system, the graphical representation of the genomic data so that at least one of the plurality of tracks shows locations of CpG islands within the genomic data for a corresponding organism.

21. The computer-implemented method of claim 1, wherein the plurality of tracks includes a fourth track that shows the first particular feature of a fourth organism; the method further comprising:
identifying, by the computing system, that the fourth organism is designated as a second reference organism; and
ordering, by the computing system and in response to identifying that the fourth organism is designated as the second reference organism and further based on the first organism being designated as the reference organism, the plurality of tracks in the graphical representation of the genomic data so that the fourth track is shown in a second reference position of the graphical representation, and the first particular features of the second and third tracks are each shown relative to both the first particular features of the first track and the first particular features of the fourth track.

22. The computer-implemented method of claim 1, wherein the first and fourth organisms are ancestors of the second and third organisms.

23. The computer-implemented method of claim 1, wherein the plurality of tracks are arranged to be displayed parallel to each other and are arranged to synchronously show corresponding portions of a chromosome sequence.

24. The computer-implemented method of claim 1, wherein identifying that the first organism is designated as the reference organism comprises receiving an indication that user input selected a control associated with the first track or the first organism.

25. The computer-implemented method of claim 1, wherein at least one of the plurality of tracks in the graphical representation of the genomic data shows a representation of recombination frequency in a chromosome sequence of an organism.

26. One or more non-transitory computer-readable devices having instructions stored thereon that, when executed by one or more processors, cause performance of operations comprising:
obtaining, by a computing system, genomic data for a plurality of organisms;
generating, by the computing system and based at least on the genomic data for the plurality of organisms, a browser plate component displaying a first graphical representation of the genomic data, the first graphical representation comprising a plurality of vertical parallel tracks that are arranged to show one or more features of the genomic data for different ones of the plurality of organisms, wherein the plurality of vertical parallel tracks includes a first track that shows a first particular feature of a first organism, a second track that shows the first particular feature of a second organism, and a third track that shows the first particular feature of a third organism; and
upon an identification, by the computing system, that the first organism is designated as a reference organism, reconfiguring, by the computing system and in response to identifying that the first organism is designated as the reference organism, the browser plate component to display a second graphical representation of the plurality of tracks in the second graphical representation of the genomic data so that the first track that shows the first particular feature of the first organism is shown in a reference position of the graphical representation, the second and third tracks are shown in respective positions proximate to the reference position, and the first particular features of the second and third tracks are each shown relative to the first particular features of the first track, wherein reconfiguring the browser plate component comprises rearranging each vertical parallel track in accordance with a rank corresponding to a similarity score between each vertical parallel track and the first track.

27. The one or more non-transitory computer-readable devices of claim 26, wherein:
the graphical representation of the genomic data is a first graphical representation of genomic data of a first chromosome; and
the operations further comprise:
generating, by the computing system, a second graphical representation of genomic data of a different, second chromosome, the second graphical representation comprising one or more tracks that are arranged to show one or more features of the genomic data of the second chromosome for at least one organism, and
outputting, by the computing system, the second graphical representation for display.

28. The one or more non-transitory computer-readable devices of claim 27, wherein the operations further comprise:
determining, by the computing system, syntenic regions of the genomic data of the first chromosome and the genomic data of the second chromosome; and
outputting, by the computing system, for display graphical elements that connect the first graphical representation and the second graphical representation, and that show corresponding syntenic regions of the genomic data of the first chromosome and the genomic data of the second chromosome.

29. The one or more non-transitory computer-readable devices of claim 26, wherein the operations further comprise identifying that user input has entered a search query associated with a particular organism; and
obtaining, by the computing system, a set of search results that are determined to be responsive to the search query, each search result in the set of search results indicating a respective chromosomal sequence location for the particular organism.

30. The one or more non-transitory computer-readable devices of claim 29, wherein the operations further comprise generating, and outputting for display, by the computing system, a graphical representation of one or more chromosomes for the particular organism that shows graphical markers at locations of the one or more chromosomes that correspond to the respective chromosomal sequence locations indicated by the set of search results.

31. The one or more non-transitory computer-readable devices of claim 29, wherein the operations further comprise receiving, by the computing system, an indication that user input selected a first search result from among the set of search results, and in response, automatically generating and outputting for display a graphical representation of the genomic data for the particular organism that shows a zoomed-in region corresponding to the location of the chromosome indicated by the first search result.

32. The one or more non-transitory computer-readable devices of claim 26,
wherein the operations further comprise:
receiving, by the computing system, an indication that the designation of the reference organism is changed from the first organism to the second organism; and
in response to receiving the indication that the designation of the reference organism is changed:
re-ordering, by the computing system, the plurality of tracks in the graphical representation of the genomic data so that the second track that shows the first particular feature of the second organism is shown in the reference position of the graphical representation, the first and third tracks are shown in respective positions outside of the reference position, and the first particular features of the first and third tracks are each shown relative to the first particular features of the second track, and
outputting, by the computing system, the re-ordered graphical representation of the genomic data for display.

33. The one or more non-transitory computer-readable devices of claim 32, wherein re-ordering the plurality of tracks in the graphical representation comprises automatically arranging the plurality of tracks in descending order of determined genetic similarity between the second organism, due to the second organism being designated as the reference organism, and the corresponding organisms for each of the other tracks in the plurality of tracks, so that tracks corresponding to organisms that are more genetically similar to the second organism are caused to be shown in closer proximity to the second track and tracks corresponding to organisms that are less genetically similar to the second organism are caused to be shown a further distance from the second track.

34. The one or more non-transitory computer-readable devices of claim 32, wherein the operations further comprise determining the genetic similarities between the second organism and the corresponding organisms for each of the other tracks in the plurality of tracks based only on data for a portion of the chromosomal sequence of the organisms currently being outputted for display.

35. The one or more non-transitory computer-readable devices of claim 26, wherein at least one of the plurality of tracks in the graphical representation shows a linear representation of codons in a chromosome sequence of an organism.

36. The one or more non-transitory computer-readable devices of claim 35, wherein at least one of the plurality of tracks is an m RNA track that shows locations of transcribed regions of the chromosome sequence.

37. The one or more non-transitory computer-readable devices of claim 26, wherein:
the first particular feature comprises single nucleotide polymorphisms (SNPs); and
the operations further comprise generating the graphical representation of the genomic data so that the second track shows, as a result of the first organism being designated as the reference organism, SNPs in the genomic data of the second organism relative to the genomic data of the first organism shown in the first track.

38. The one or more non-transitory computer-readable devices of claim 37, wherein the second track shows SNPs in the genomic data of the second organism relative to the genomic data of the first organism by showing colored elements along the second track at locations that correspond to locations in a chromosome sequence where SNPs occur that are opposite of SNPs in the genomic data of the first organism.

39. The one or more non-transitory computer-readable devices of claim 26, wherein the operations further comprise obtaining, at the computing system, data that indicates expression levels for corresponding portions of the genomic data for one or more of the plurality of organisms.

40. The one or more non-transitory computer-readable devices of claim 39, wherein:
   the first particular feature comprises the expression levels for the corresponding portions of the genomic data,
   the operations further comprise generating the graphical representation of the genomic data so that the second track shows, as a result of the first organism being designated as the reference organism, expression levels for the corresponding portions of the genomic data of the second organism relative to the expression levels of for the corresponding portions of the genomic data of the first organism.

41. The one or more non-transitory computer-readable devices of claim 40, wherein the second track shows allele-specific expression levels.

42. The one or more non-transitory computer-readable devices of claim 39, wherein the operations further comprise:
   generating, by the computing system and based at least on the data that indicates the expression levels for the corresponding portions of the genomic data for the one or more of the plurality of organisms, a multidimensional plot showing variability in expression levels among different sets of expression data for particular ones of the plurality of organisms; and
   outputting, by the computing system, the multidimensional plot for display.

43. The one or more non-transitory computer-readable devices of claim 42, wherein generating the multidimensional plot comprises automatically limiting the plot to showing only expression levels of sequences corresponding to a portion the genomic data being outputted for display in the graphical representation of the genomic data, to the exclusion of expression levels of sequences outside of the portion of the genomic data being outputted for display in the graphical representation of the genomic data.

44. The one or more non-transitory computer-readable devices of claim 26, wherein the first particular feature comprises at least one of quantitative trait loci (QTLs) and trait linkage scores for particular sequence locations.

45. The one or more non-transitory computer-readable devices of claim 26, wherein:
   the first particular feature comprises CpG islands; and
   the operations further comprise generating, by the computing system, the graphical representation of the genomic data so that at least one of the plurality of tracks shows locations of CpG islands within the genomic data for a corresponding organism.

46. The one or more non-transitory computer-readable devices of claim 26, wherein the plurality of tracks includes a fourth track that shows the first particular feature of a fourth organism;
   the method wherein the operations further comprise:
   identifying, by the computing system, that the fourth organism is designated as a second reference organism; and
   ordering, by the computing system and in response to identifying that the fourth organism is designated as the second reference organism and further based on the first organism being designated as the reference organism, the plurality of tracks in the graphical representation of the genomic data so that the fourth track is shown in a second reference position of the graphical representation, and the first particular features of the second and third tracks are each shown relative to both the first particular features of the first track and the first particular features of the fourth track.

47. The one or more non-transitory computer-readable devices of claim 26, wherein the first and fourth organisms are ancestors of the second and third organisms.

48. The one or more non-transitory computer-readable devices of claim 26, wherein the plurality of tracks are arranged to be displayed parallel to each other and are arranged to synchronously show corresponding portions of a chromosome sequence.

49. The one or more non-transitory computer-readable devices of claim 26, wherein identifying that the first organism is designated as the reference organism comprises receiving an indication that user input selected a control associated with the first track or the first organism.

50. The one or more non-transitory computer-readable devices of claim 26, wherein at least one of the plurality of tracks in the graphical representation of the genomic data shows a representation of recombination frequency in a chromosome sequence of an organism.

51. A computer program product, stored on one or more non-transitory computer-readable devices, for analyzing and representing genome-related biological data, the program product including:
   a genotype tracks module configured to generate and output for display a graphical user interface comprising a browser plate component displaying one or more vertical parallel tracks showing features of genomic data for corresponding organisms;
   a similarity analyzer configured to determine similarities between corresponding portions of genetic sequences for a reference organism and two or more additional organisms; and
   a track arrangement module configured to reconfigure the display of the one or more vertical parallel tracks, wherein the track arrangement module reconfigures the display such that a first track corresponding to the reference organism is displayed in a reference position and the two or more additional organisms are displayed based on the determined similarities between the corresponding portions of genetic sequences for the reference organism and the two or more additional organisms, wherein the reconfiguring comprises rearranging each vertical parallel track in accordance with a rank corresponding to a similarity score between each vertical parallel track and the first track.

52. The computer program product of claim 51, further comprising a search module configured to receive queries from user input, and to identify search results that are determined to be responsive to the queries in that the search results correspond to candidate locations in a chromosomal sequence for particular organisms associated with the queries.

* * * * *